(12) United States Patent
Ladipo et al.

(10) Patent No.: US 7,851,570 B2
(45) Date of Patent: Dec. 14, 2010

(54) PRECATALYSTS USEFUL IN POLYOLEFIN POLYMERIZATION REACTIONS

(75) Inventors: Omofolami Tesileem Ladipo, Lexington, KY (US); Richard Eaves, Lexington, KY (US); Alexey Zazybin, Kazan (RU); Sean Parkin, Lexington, KY (US)

(73) Assignee: The University of Kentucky Research Foundation, Lexington, KY (US)

( * ) Notice: Subject to any disclaimer, the term of this patent is extended or adjusted under 35 U.S.C. 154(b) by 895 days.

(21) Appl. No.: 11/710,174

(22) Filed: Feb. 23, 2007

(65) Prior Publication Data

US 2008/0207853 A1    Aug. 28, 2008

(51) Int. Cl.
*C08F 4/64* (2006.01)
*B01J 31/18* (2006.01)
*B01J 31/22* (2006.01)
*C08F 4/642* (2006.01)

(52) U.S. Cl. .................. 526/161; 526/159; 526/165; 526/172; 526/348; 502/103; 502/167; 502/168; 502/171

(58) Field of Classification Search ............... 526/159, 526/161, 172; 502/103, 167, 168, 171
See application file for complete search history.

(56) References Cited

PUBLICATIONS

Gamaz, Patrick et al., Synthesis and catalytic activities of copper (II) complexes derived from a tridentate pyrazole-containing ligand. X-ray crystal structure of [Cu2(u-dpzh-O,N,N')2][Cu(MeOH)Cl3]2, Inorganica Chimica Acta, 324 (2001) 27-34, Elsevier Science B.V.

*Primary Examiner*—Caixia Lu
(74) *Attorney, Agent, or Firm*—King & Schickli, PLLC

(57) ABSTRACT

Compounds are provided that are useful as precatlysts in the polymerization of olefins such as ethylene and propylene. Other compounds are useful as intermediates in the production of such precatalysts.

11 Claims, No Drawings

PRECATALYSTS USEFUL IN POLYOLEFIN POLYMERIZATION REACTIONS

TECHNICAL FIELD AND INDUSTRIAL APPLICABILITY OF THE INVENTION

The present invention relates generally to the polymerization catalyst field and, more particularly to precatalysts useful in polyolefin polymerization reactions and ligand intermediants useful in the production of those precatalysts.

BACKGROUND OF THE INVENTION

Polymers of polyolefins including, for example, ethylene and propylene are made in enormous quantities for many commercial uses. A number of methods are known for polymerizing olefins. Such methods include free radical polymerization of ethylene, coordination polymerization using catalysts such as Ziegler-Natta-type and metallocene-type catalysts and single site catalysts using late transition metal complexes. In view of the importance of polyolefins, new precatalysts and catalysts are constantly being sought for such polymerizations with the hope that they will lower the cost of production and/or make new and improved polymer structures.

The present invention relates to novel precatalysts useful in olefin polymerization reactions as well as ligand intermediates useful in the production of those precatalysts.

SUMMARY OF THE INVENTION

In accordance with the purposes of the present invention, a series of compounds are provided with the formula:

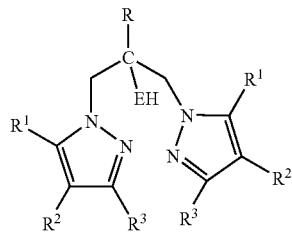

(Formula 1)

where E=O or S and R, $R^1$, $R^2$, and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen.

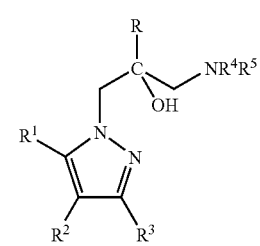

(Formula 2)

where R, $R^1$, $R^2$, $R^3$, $R^4$ and $R^5$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen.

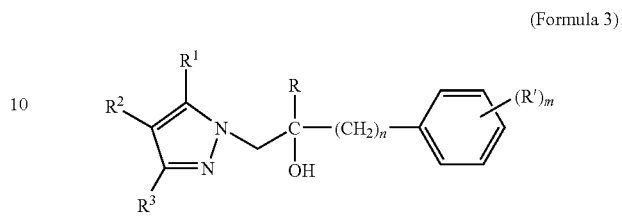

(Formula 3)

where R, $R^1$, $R^2$ and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=a branched or linear alkyl group, n=1 or 2 and m=0-5. Such compounds are particularly useful in the production of precatalysts for olefin polymerization reactions.

In accordance with an additional aspect of the present invention, novel compounds or precatalysts are provided with the formula

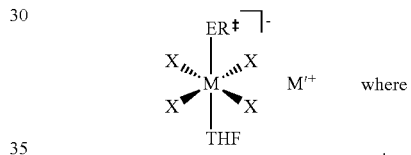

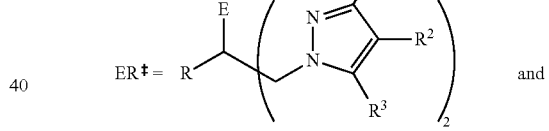

(Formula 4)

M=Ti, Zr or Hf, E=O or S, R, $R^1$, $R^2$ and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, X=halogen, and $M'^+$=an alkali metal ion or any monopositive cation.

Alternatively, the compounds or precatalysts may have the formula

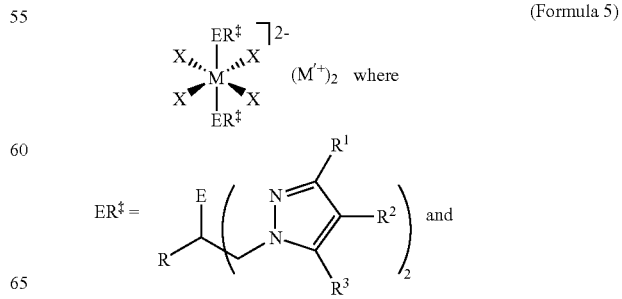

(Formula 5)

M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, X=halogen, and $M'^+$=an alkali metal ion or any monopositive cation; $(M'^+)_2$=any dipositive cation.

In yet another alternative the compound or precatalyst may have the formula

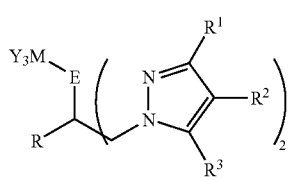

(Formula 6)

where M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

In yet another alternative the compound or precursor may have the formula

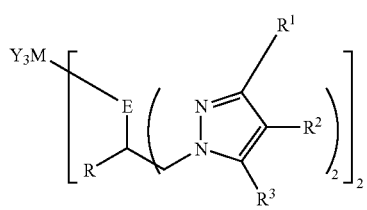

(Formula 7)

where M=Ti, Zr or Hf, E=O or S, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

In still another embodiment the compound or precatalyst may have the formula

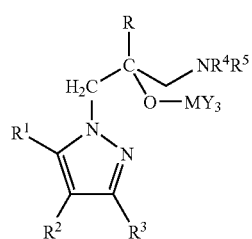

(Formula 8)

where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

Still further the compound or precatalyst may have the formula

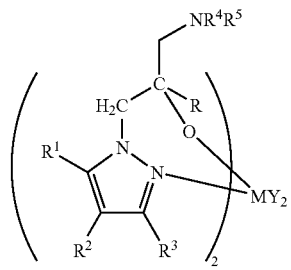

(Formula 9)

Where M=Ti, Zr or Hf, R, $R^1$, $R^2$, $R^3$, $R^4$ and $R^5$ are hydrogen, a branched or linear alkyl group, a branched or linear alkynyl group, a cycloalkyl group, a cycloalkenyl group, an alkoxy group, an aryl group, a silyl group, a halogen, and Y=an anionic monodentate ligand.

In yet another embodiment the compound or precatalyst may have the formula

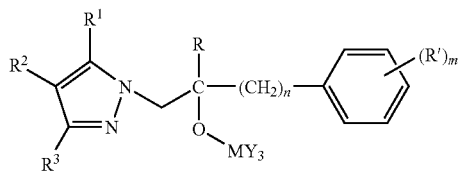

(Formula 10)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=an aryl group, a silyl group, halogen, an alkoxo group, or amido group, m=0-5, n=1 or 2 and Y=an anionic monodentate ligand.

In an additional embodiment the compound or precatalyst may have the formula

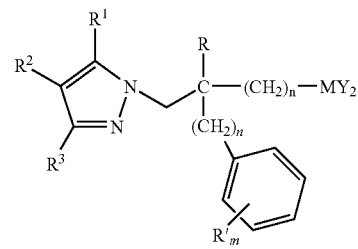

(Formula 11)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=an aryl group, a silyl group, halogen, an alkoxo group, or amido group, m=0-5, n=1 or 2 and Y=an anionic monodentate ligand.

In yet another embodiment the compound or precatalyst may have the formula

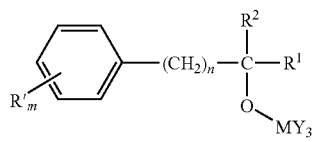
(Formula 12)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=an aryl group, a silyl group, halogen, an alkoxo group, or amido group, m=0-5, n=1 or 2 and Y=anionic monodentate ligand.

In still another embodiment the compound or precatlyst may have the formula

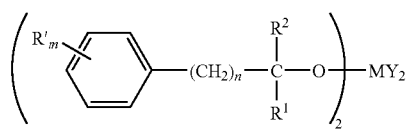
(Formula 13)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=an aryl group, a silyl group, halogen, an alkoxo group, or amido group, m=0-5, n=1 or 2 and Y=anionic monodentate ligand.

In accordance with yet another aspect of the present invention a method of making a precatalyst is provided. That method comprises reacting a compound of formulas 1, 2 or 3 with a Group IV B metal.

In still another aspect of the present invention a method of polymerizing an olefin comprises conducting a polymerization reaction of said olefin in the presence of a catalyst formed by a precatalyst of any of formulas 4-13.

DETAILED DESCRIPTION OF THE INVENTION

In accordance with the present invention, a series of compounds are provided that are useful as intermediates in the preparation of precatlysts for olefin polymerization reactions. These compounds have the following formula:

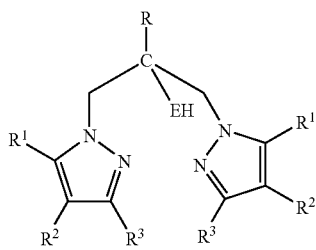
(Formula 1)

where E=O or S and R, $R^1$, $R^2$, and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen;

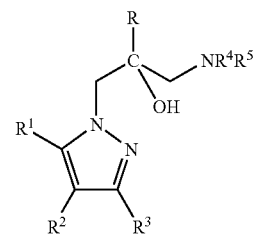
(Formula 2)

where R, $R^1$, $R^2$, $R^3$, $R^4$ and $R^5$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen;

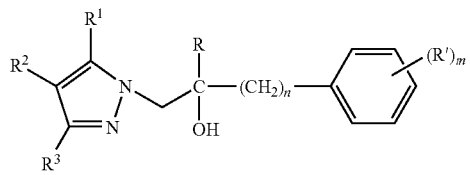
(Formula 3)

where R, $R^1$, $R^2$ and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=a branched or linear alkyl group, an aryl group, a silyl group, halogen, an alkoxo group, or amido group, n=1 or 2 and m=0-5. Such compounds are particularly useful in the production of precatalysts for olefin polymerization reactions.

In accordance with an additional aspect of the present invention, novel compounds or precatalysts are provided with the formula

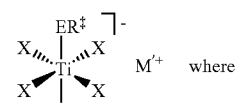
(Formula 4)

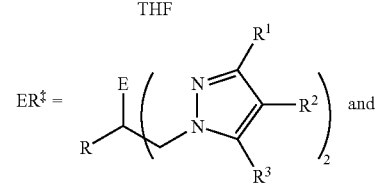

M=Ti, Zr or Hf, E=O or S, R, $R^1$, $R^2$ and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, X=halogen, and M'+=an alkali metal ion or any monopositive cation.

Alternatively, the compounds or precatalysts may have the formula

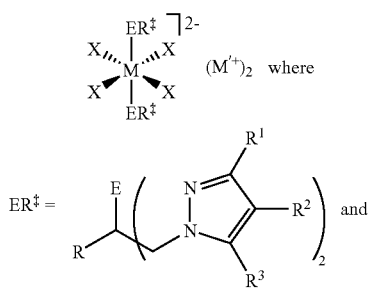

(Formula 5)

M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, X=halogen, and M'+=an alkali metal ion or any monopositive cation; $(M'^+)_2$=any dipositive cation.

In yet another alternative the compound or precatalyst may have the formula

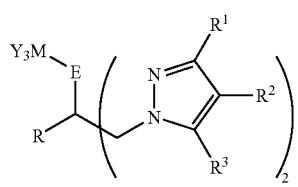

(Formula 6)

where M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

In yet another alternative the compound or precursor may have the formula

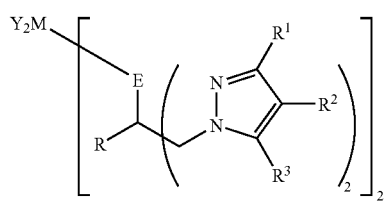

(Formula 7)

where M=Ti, Zr or Hf, E=O or S, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

In still another embodiment the compound or precatalyst may have the formula

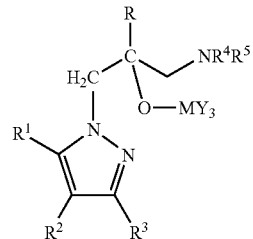

(Formula 8)

where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

Still further the compound or precatalyst may have the formula

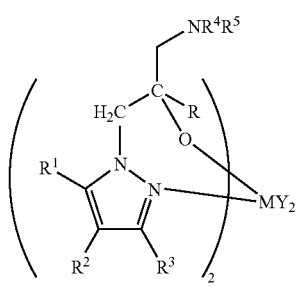

(Formula 9)

Where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, and Y=an anionic monodentate ligand.

In yet another embodiment the compound or precatalyst may have the formula

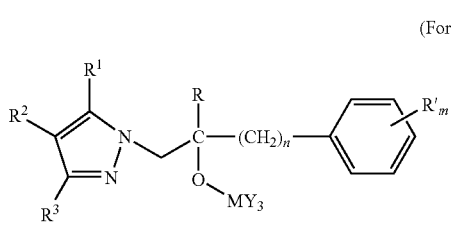

(Formula 10)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=a branched or linear alkyl group, an aryl group, a silyl group, halogen, an alkoxo group, or amido group m=0-5, n=1 or 2 and Y=an anionic monodentate ligand.

In an additional embodiment the compound or precatalyst may have the formula

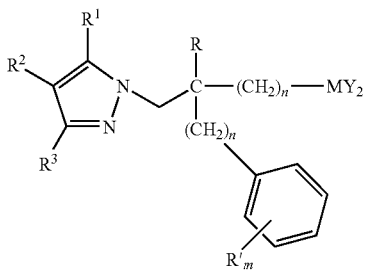

(Formula 11)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=a branched or linear alkyl group, an aryl group, a silyl group, halogen, an alkoxo group, or amido group, m=0-5, n=1 or 2 and Y=an anionic monodentate ligand.

In yet another embodiment the compound or precatalyst may have the formula

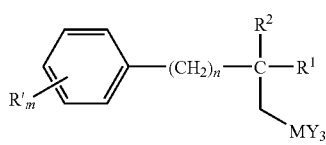

(Formula 12)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=a branched or linear alkyl group, an aryl group, a silyl group, halogen, an alkoxo group, or amido group, m=0-5, n=1 or 2 and Y=anionic monodentate ligand.

In still another embodiment the compound or precatlyst may have the formula

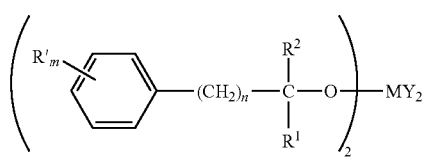

(Formula 13)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, a halogen, R'=a branched or linear alkyl group, an aryl group, a silyl group, halogen, an alkoxo group, or amido group, m=0-5, n=1 or 2 and Y=anionic monodentate ligand.

Synthesis of the compounds or ligands of formula 1-3 are presented in examples 1-3. The compounds of formulas 1-3 are particularly useful in the production of the precatalysts of the present invention. More specifically, the compounds of formulas 1-3 are reacted with a Group IV B metal to form the catalysts. These reactions may be generally described as follows.

Compounds of formula 1. Reaction of sodium hydride with appropriate 1H-pyrazole starting material in ethereal solution and at low temperature furnishes the corresponding pyrazol-1-yl anion, which then reacts in 2:1 molar ratio with 1,3-dichloropropan-2-ol to give the corresponding 1,3-bis(pyrazol-1yl)propan-2-ol compound. After suitable work-up (typically column chromatography), the product is obtained in pure form.

Compounds of formula 2. Reaction of sodium hydroxide with appropriate 1H-pyrazole starting material in neat epichlorohydrin at room temperature furnishes the corresponding 1-oxiranylmethyl-1H-pyrazole compound. To this product is added distilled water and an excess of secondary amine. The reaction mixture is then heated at moderate to high temperature (~80° C.) for several hours. After suitable work-up (typically column chromatography), the corresponding 1-amino-3-(pyrazol-1-yl)-propan-2-ol compound is isolated.

Compounds of formula 3. Reaction of sodium hydroxide with appropriate 1H-pyrazole starting material in ethereal solvent furnishes the corresponding pyrazol-1-yl anion, which reacts with suitable 1-chloro-3-arylpropan-2-ol- or 1-chloro-4-arylbutan-2-ol compound to give the corresponding product of formula 3.

Specific examples of the production of precatalysts of formulas 4-13 are presented in examples 4-13.

For purposes of this document, a "precatalyst" may be defined as the catalyst precursor; the compound from which the catalyst is derived. In addition, the reactions may be generally described as follows.

Formula 4 and 5 precatalysts are formed via addition reaction of $MX_4$ compounds (M=Ti, Zr or Hf; X=halogen) with 1:1 or 1:2 molar ratio of M'E$_R$ salts in ethereal solvent at low- to room temperatures (H-E$_R$=compounds of formula 1; M'$^+$=an alkali metal ion or any monopositive cation; (M'$^+$)$_2$ = any dipositive cation). The compounds are isolated as pure solids after work-up from THF.

Formula 6-13 precatalysts are formed by direct- or base-assisted protonolysis reaction of $MY_4$ compounds (M=Ti, Zr or Hf; Y=anionic monodentate ligand) with 1:1 or 1:2 molar ratio of compounds of formula 1, 2, or 3 in hydrocarbon solvent at low- or room temperature. The compounds are isolated as pure solids after appropriate work-up (typically, filtration followed by recrystallization).

The precatalysts of formulas 4-13 are all useful in processes for polymerizing olefins such as ethylene and propylene. This is accomplished by conducting a polymerization reaction of the olefin in the presence of a catalyst formed by activation of the precatalysts. A typical procedure for the polymerization of ethylene is set forth in example 14. Example 15 presents comparative data illustrating the catalytic activity resulting from use of the precatalyst in the polymerization reaction of ethylene in the manner set forth in example 14, compared to other catalysts known to be useful for this purpose.

The following synthesis and examples are presented to further illustrate the invention. The invention is not to be considered as limited thereto.

EXPERIMENTAL

General details: All experiments were performed under dry nitrogen atmosphere using standard Schlenk techniques or in a Vacuum Atmospheres, Inc. glovebox. Solvents were dried and distilled by standard methods before use. All solvents were stored in the glovebox over 4A molecular sieves that were dried in a vacuum oven at 150° C. for at least 48 hours prior to use. Unless otherwise stated, all reagents were purchased from Aldrich Chemical Company. Ethylene (99.9% purity) was purchased from Scott-Gross Co. or Matheson Tri-Gas Inc.

Example 1

1,3-bis(3,5-di-tert-butylpyrazol-1yl)propan-2-ol {(bdb-pzp)H}. 3,5-Di-tert-butyl-1H-pyrazole (20.0 g, 111 mmol) was added slowly to a suspension of sodium hydride (4.39 g, 183 mmol) in diethyl ether (200 mL) at 0° C. The reaction mixture was refluxed with stirring for 1 h then cooled to 0° C. 1,3-Dichloropropan-2-ol (5.30 mL, 55.0 mmol) was added dropwise and the mixture was refluxed for 3 days. The reaction mixture was cooled to 0° C., quenched by the addition of water (5 ml), and extracted with diethyl ether (5×20 mL). The ether extracts were combined and washed with water followed by brine. The ether solution was dried over anhydrous MgSO$_4$, filtered, and then concentrated to dryness. 1,3-Bis(3,5-di-tert-butylpyrazol-1-yl)propan-2-ol (formula 14) was isolated as a white powder following flash chromatography on silica using 3% CH$_2$Cl$_2$ in methanol as eluent. Yield: 12.6 g, 55%. $^1$H (CDCl$_3$): δ 1.26 (s, 36H, Bu$^t$), 4.17-4.28 (m, 3H, CH$_2$, CH), 4.46-4.58 (m, 2H, CH$_2$), 5.80 (s, 2H, pyz-4), 6.26 (br s, 1H, OH). $^{13}$C (CDCl$_3$): δ 30.1, 30.5, 31.2, 31.9, 53.3, 71.7, 99.5, 152.0, 160.1. MS (EI, 70 eV) m/z: 398 [M-H$_2$O]$^+$.

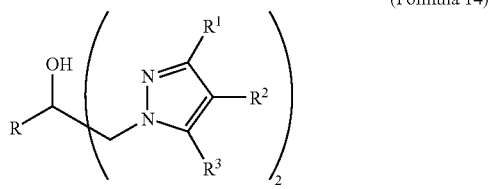

(Formula 14)

R = R$^2$ = H, R$^1$ = R$^3$ = Bu$^t$; (b dbpzp)H

Example 2

General Synthesis of 1-Dialkylamino-3-(3,5-dimethyl-pyrazol-1-yl)-propan-2-ols NaOH pellets (7.50 g, 0.188 mol) were added into a slightly heterogeneous mixture of 3,5-dimethylpyrazole (15.0 g, 0.156 mol) and epichlorohydrin (250 ml, 3.19 mol). After stirring for several minutes, NaCl began to precipitate and the reaction mixture was stirred at room temperature for 24 h. The resulting suspension was then filtered and the filtrate was evaporated under reduced pressure to give 3,5-dimethyl-1-oxiranylmethyl-1H-pyrazole as a viscous oil. This crude product, which contained 5-10% (by GC-MS) of 1,3-bis(3,5-dimethyl-1H-pyrazol-1-yl)propan-2-ol, was used in the preparation of the following compounds without purification.

1-Diisopropylamino-3-(3,5-dimethyl-pyrazol-1-yl)-propan-2-ol [(Pr$^i_2$-admpzp)H]. Distilled water (2.00 mL, 0.156 mol) and Pr$^i_2$NH (65.6 mL, 0.468 mol) were added to the viscous oil of 3,5-dimethyl-1-oxiranylmethyl-1H-pyrazole and the resulting solution was stirred at reflux for 3 h. After cooling to room temperature, the solution was concentrated under reduced pressure to give a brown-yellow viscous oil. This crude product was purified by column chromatography using a 35:4:1 ethyl acetate:hexane:triethylamine mixture as eluent. The solution was evaporated under reduced pressure to give 1-Diisopropylamino-3-(3,5-dimethyl-pyrazol-1-yl)-propan-2-ol [(Pr$^i_2$-admpzp)H] (formula 15A) as a white powder. Yield: 21.7 g, 55%. $^1$H NMR (C$_6$D$_6$): δ 5.71 (s, 1H, pyz-4), 4.39 (s, 1H, CH—OH), 4.03 (dd, $^2$J=13.8 Hz, $^3$J=4 Hz, 1H, H$_A$ of —CH$_2$pyz), 3.91 (m, 1H, HO—CH), 3.73 (dd, $^2$J=13.8 Hz, $^3$J=8.5 Hz, 1H, H$_B$ of —CH$_2$pyz), 2.72 (sept, $^3$J=8.5 Hz, 2H, N{CHMe$_2$}$_2$), 2.44 (dd, $^2$J=17 Hz, 1H, H$_A$ of —CH$_2$NPr$^i_2$), 2.42 (dd, J=17 Hz, 1H, (H$_B$ of —CH$_2$NPr$^i_2$), 2.25 (s, 3H, CH$_3$ at pyz-3), 2.07 (s 3H, CH$_3$ at pyz-5), 0.81 (d, $^3$J=8.5 Hz, 6H, N—CHMe$_2$), 0.77 (d, 6H, $^3$J=8.5 Hz, N—CHMe$_2$). $^{13}$C NMR (C$_6$D$_6$): δ 147.0 (pyz-3), 139.7 (pyz-5), 104.8 (pyz-4), 68.6 (CH—OH), 52.6 (CH$_2$pyz), 48.4 (N{CHMe$_2$}$_2$), 48.3 (CH$_2$NPr$^i_2$), 21.4 (N—CHMe$_2$), 20.3 (N—CHMe$_2$), 13.8 (CH$_3$ at pyz-3), 11.1 (CH$_3$ at pyz-5). IR (Nujol, cm$^{-1}$): 3136, 1552, 1465, 1384, 1360, 1333, 1296, 1191, 1176, 1128, 1096, 974, 885, 787. GC-MS(EI): M$^+$ (253).

1-Dibenzylamino-3-(3,5-dimethyl-pyrazol-1-yl)-propan-2-ol [(Bn$_2$-admpzp)H] Prepared as described for (Pr$^i_2$-admpzp)H except using dibenzylamine (30 mL, 0.156 mol) and heating the reaction mixture at 80° C. for 3 h. (Bn$_2$-admpzp)H (formula 15B) was isolated as a white powder. Yield: 30.5 g, 56%. $^1$H NMR (C$_6$D$_6$): δ 7.22-7.04 (m, 10H, N(CH$_2$Ph)$_2$), 5.64 (s, 1H, pyz-4), 4.61 (d, $^3$J=2.5 Hz, 1H, CH—OH), 4.12 (m, 1H, HO—CH), 3.82 (dd, $^2$J=17 Hz, $^3$J=3.5 Hz, 1H, H$_A$ of —CH$_2$pyz), 3.56 (dd, $^2$J=17 Hz, $^3$J=9.5 Hz, 1H, H$_B$ of —CH$_2$pyz), 3.43 (d, $^2$J=17 Hz, 2H, H$_A$ of CH$_2$Ph), 3.39, d, $^2$J=17 Hz, 2H, H$_B$ of CH$_2$Ph), 2.54 (dd, $^2$J=16.5 Hz, 1H, H$_A$ of —CH$_2$NPr$^i_2$), 2.52 (dd, $^2$J=16.5 Hz, 1H, H$_B$ of —CH$_2$NPr$^i_2$), 2.20 (s, 3H, CH$_3$ at pyz-3), 1.82 (s, 3H, CH$_3$ at pyz-5). $^{13}$C NMR (C$_6$D$_6$): δ 147.4 (pyz-3), 139.5 (pyz-5), 139.3, 129.3, 128.5, 127.3, 104.8 (pyz-4), 69.1 (CH—OH), 59.1 (CH$_2$Ph), 57.0 (CH$_2$N(CH$_2$Ph)$_2$), 52.1 (CH$_2$pyz), 13.7 (CH$_3$ at pyz-3), 10.5 (CH$_3$ at pyz-5). IR (Nujol, cm$^{-1}$): 3174, 1548, 1461, 1377, 1359, 1123, 1092, 1077, 1047, 1032, 910, 860, 782, 751, 736, 699. GC-MS(EI): M$^+$ (349).

1-(Benzyl-tert-butyl-amino)-3-(3,5-dimethyl-pyrazol-1-yl)-propan-2-ol [(Bu$^t$Bn-admpzp)H]. Prepared as described for (Bn$_2$-admpzp)H using benzyl-tert-butylamine (28.3 mL, 0.156 mol). (Bu$^t$Bn-admpzp)H (formula 15C) was isolated as a yellow liquid. Yield: 18.7 g, 38%. $^1$H NMR (C$_6$D$_6$): δ 7.20-6.98 (m, 5H, CH$_2$Ph) 5.60 (s, 1H, pyz-4), 4.24 (br s, 1H, CH—OH), 3.83 (dd, $^2$J=17 Hz, $^3$J=4 Hz, 1H, H$_a$ of —CH$_2$pyz), 3.64 (m, 1H, HO—CH), 3.41 (dd, $^2$J=17 Hz, $^3$J=8.5 Hz, 1H, H$_B$ of —CH$_2$pyz), 3.46 (d, $^2$J=18.5 Hz, 1H, H$_A$ of CH$_2$Ph), 3.35 (d, $^2$J=18.5 Hz, 1H, H$_B$ of CH$_2$Ph), 2.74 (dd, $^2$J=17 Hz, $^3$J=9 Hz, 1H, H$_A$ of CH$_2$NBu$^t$Bn), 2.52 (dd, $^2$J=17 Hz, $^3$J=8.5 Hz, 1H, H$_B$ of CH$_2$NBu$^t$Bn), 2.13 (s, 3H, CH$_3$ at pyz-3), 1.85 (s, 3H, CH$_3$ at pyz-5), 0.89 (s, 9H, Bu$^t$). $^{13}$C NMR(C$_6$D$_6$): δ 147.0 (pyz-3), 139.5 (pyz-5), 142.9, 128.5, 128.1, 126.8, 104.7 (pyz-4), 70.0 (CH—OH), 55.9 (CH$_2$Ph), 55.5 (N—CMe$_3$), 55.1 (CH$_2$NBu$^t$Bn), 52.0 (CH$_2$pyz), 27.2 (N—CMe$_3$), 13.7 (CH$_3$ at pyz-3), 11.0 (CH$_3$ at pyz-5). IR (Neat, cm$^{-1}$): 3381, 3027, 2970, 2870, 1553, 1493, 1467, 1425, 1391, 1364, 1258, 1245, 1199, 1123, 1055, 1026, 948, 900, 842, 774, 750, 735, 715, 699. GC-MS(EI): M⁺ (315).

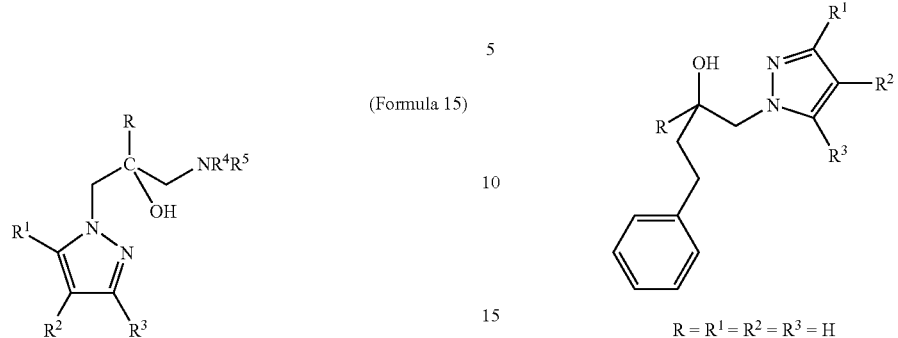

(Formula 15)

A.) R=R²=H, R¹=R³=Me, R⁴=R⁵=Pr$^i$; (Pr$^i_2$-admpzp)H
B.) R=R²=H, R¹=R³=Me, R⁴=R⁵=CH₂Ph; (Bn₂-admpzp)H
C.) R=R²=H, R¹=R³=Me, R⁴=Bu$^t$, R⁵=CH₂Ph; (Bu$^t$Bn-admpzp)H Example 3

1-Phenyl-3-pyrazol-1-yl-propan-2-ol [(Phdmpzp)H] (formula 16). Dimethylpyrazole (1.64 g, 17 mmol) was added to a pre-cooled solution of sodium hydride (818 mg, 34 mmol) in THF at 0° C. The reaction was allowed to warm to room temperature and stirred for 2 h. The solution was then cooled to 0° C., and 1-chloro-3-phenylpropan-2-ol (1.45 g, 9 mmol) was added dropwise. The reaction was then heated to reflux for 36 h, and then cooled to 0° C. Water (5 mL) was added dropwise, and then the organic layers were washed with water (2×20 mL) and then brine (2×20 mL), and dried over magnesium sulfate. Flash column chromatography gave 1-phenyl-3-pyrazol-1-yl-propan-2-ol. Yield: 0.56 g, 33%.

(Formula 16)

R = R¹ = R² = R³ = H

1-Phenyl-3-(3,5-dimethyl-pyrazol-1-yl)-propan-2-ol; (Phdmpzp)H 4-Phenyl-1-pyrazol-1-yl-butan-2-ol [(Phdmpzb)H] (formula 17). This compound was prepared as described above except 1-chloro-4-phenylbutan-2-ol was utilized in place of 1-chloro-3-phenylpropan-2-ol.

(Formula 17)

R = R¹ = R² = R³ = H

4-Phenyl-1-(3,5-dimethyl-pyrazol-1-yl)-butan-2-ol; (Phdmpzb)H

Example 4

Na[(bdbpzp)(THF)TiCl₄] (1a) (formula 18). To a suspension of sodium hydride (58.0 mg, 2.40 mmol) in ether (50 mL) was added 1,3-bis(3,5-di-tert-butylpyrazol-1-yl)propan-2-ol (1.00 g, 2.40 mmol). The reaction was refluxed for 2 h then cooled to room temperature and the suspension was transferred into an addition funnel. The suspension was added dropwise to a cold (0° C.) solution of TiCl₄ (0.45 g, 2.40 mmol) in ether (50 mL). After the addition was complete, the reaction mixture was stirred for 1 h at 0° C. then allowed to warm gradually to ambient temperature and let stir overnight. The suspension was concentrated to dryness and the residue was exhaustively extracted with THF (~100 mL). The solvent was removed under reduced pressure and the pale yellow solid was dried under vacuum. Yield: 1.08 g, 71.6%. ¹H (CDCl₃): δ 1.42 (s, 18H, Bu$^t$), 1.44 (s, 18H, Bu$^t$), 1.92 (m, 4H, THF), 4.20 (br m, 4H, THF), 4.53-5.41 (br, m, 5H, CH₂, CH), 6.10 (s, 2H, pyz-4). ¹³C (CDCl₃): δ 25.5 (THF) 30.1, 30.3, 32.4, 32.5, 52.8, 71.5 (THF), 102.6, 157.0, 159.6. LDI-TOF MS (negative ion mode, m/z): 518 [C₃H₅Cl₉Na₂OTi₂]⁻, 483 [C₃H₅Cl₈Na₂OTi₂]⁻, 388 [C₃H₅Cl₆NaOTi₂]⁻, 353 [C₃H₅Cl₅NaOTi₂]⁻, 295 [C₃H₅Cl₄OTi₂]⁻, 258 [C₃H₅Cl₃OTi₂]⁻, 223 [C₃H₅Cl₂OTi₂]⁻. Anal. Calcd. for C₂₉H₅₁Cl₄N₄NaO₂Ti: C, 49.73; H, 7.34; N, 8.00. Found: C, 49.17; H, 7.40; N, 7.49.

Na[(bdmpzp)(THF)TiCl₄] (1b) (formula 18). To a diethyl ether (100 mL) suspension of sodium hydride (0.090 g, 3.75 mmol) was added 1,3-bis(3,5-dimethylpyrazol-1-yl)propan-2-ol (0.93 g, 3.75 mmol). The reaction mixture was heated at reflux for 2 h then cooled to room temperature and the suspension was transferred into an addition funnel. The suspension was added dropwise to a cold (0° C.) solution of TiCl₄ (0.73 g, 3.75 mmol) in diethyl ether (50 mL). After the addition was complete, the reaction was stirred for 1 h at 0° C. then allowed to warm gradually to ambient temperature and let stir overnight. The suspension was concentrated to dryness and the residue was exhaustively extracted with THF (~100 mL). The solvent was removed under reduced pressure and the pale yellow solid was dried under vacuum. Yield: 1.38 g, 80.0%. ¹H (CD₃CN): δ 1.80 (m, 4H, THF), 2.43 (br s, 6H, CH₃), 2.46 (br s, 6H, CH₃), 3.66 (m, 4H, THF), 4.35-4.91 (m, 5H, CH₂, CH), 6.23 (s, 2H, pyz-4). ¹³C (CD₃CN); δ 11.8, 26.3 (THF), 51.5, 68.5 (THF), 108.3, 147.2. IR (CH₃CN): ν(Ti—O) 688 cm⁻¹. LDI-TOF MS (negative ion mode, m/z): 540 [Na₂Ti₂Cl₈{OCH(CH₂)₂}₂]⁻, 460 [NaTi₂Cl₈{OCH(CH₂)₂}]⁻, 404 [C₃H₅Cl₆NaO₂Ti₂]⁻, 324 [Cl₆OTi₂]⁻, 305

[Cl$_5$O$_2$Ti$_2$]$^-$, 270 [C$_3$H$_5$Cl$_4$NaOTi]$^-$, 190 [TiCl$_4$]$^-$, 169 [Cl$_3$OTi]$^-$. Anal. Calcd. for C$_{17}$H$_{27}$Cl$_4$N$_4$NaO$_2$Ti: C, 38.37; H, 5.11; N, 10.53. Found: C, 39.03; H, 5.39; N, 9.89.

(Formula 18)

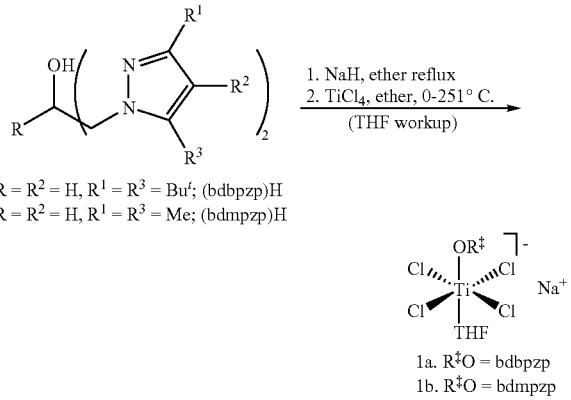

R = R$^2$ = H, R$^1$ = R$^3$ = Bu$^t$; (bdbpzp)H
R = R$^2$ = H, R$^1$ = R$^3$ = Me; (bdmpzp)H 1. NaH, ether reflux
2. TiCl$_4$, ether, 0-251° C.
(THF workup)

1a. R$^\ddagger$O = bdbpzp
1b. R$^\ddagger$O = bdmpzp

Example 5

[Na(THF)]$_2$[(bdbpzp)$_2$TiCl$_4$] (2a) (formula 19). To a suspension of sodium hydride (0.058 g, 2.40 mmol) in ether (50 mL) was added 1,3-bis(3,5-di-tert-butylpyrazol-1-yl)propan-2-ol (1.00 g, 2.40 mmol). The reaction was refluxed for 2 h then cooled to room temperature and the suspension was transferred into an addition funnel. The suspension was added dropwise to a cold (0° C.) solution of TiCl$_4$ (0.225 g, 1.19 mmol) in ether (50 mL). After the addition was complete, the reaction mixture was stirred for 1 h at 0° C. then allowed to warm gradually to ambient temperature and let stir overnight. The suspension was concentrated to dryness and the residue was exhaustively extracted with THF (~100 mL). The solvent was removed under reduced pressure and the pale yellow solid was dried under vacuum. Yield: 0.955 g, 77.3%. Compound 2a typically co-crystallizes with two THF molecules, which can be removed to different extents under vacuum. For 1.2THF: $^1$H (CDCl$_3$) δ: 1.34 (s, 36H, Bu$^t$), 1.37 (36H, Bu$^t$), 1.83 (m, 4H, THF), 3.81 (br m, 4H, THF), 4.32-5.13 (br m, 10H, CH$_2$, CH), 5.96 (s, 4H, pyz-4). $^{13}$C (CDCl$_3$) δ: 25.8 (THF), 30.2 (CH(CH$_3$)$_3$), 30.3 (CH(CH$_3$)$_3$), 31.9 (CH (CH$_3$)$_3$), 32.3 (CH(CH$_3$)$_3$), 53.2 (OCH(CH$_2$-pyz)$_2$), 70.1 (THF), 101.2 (OCH(CH$_2$-pyz)$_2$), 155.0, 159.7. EI-MS (m/z): 913 [(bdbpzp)$_2$TiCl]$^+$; LDI-TOF MS (negative ion mode, m/z): as [TiCl$_4$]$^-$ (m/z=190), [NaTiCl$_4${OCH(CH$_2$)$_2$}]$^-$ (m/z=270), [Na$_2$Ti$_2$Cl$_8${OCH(CH$_2$)$_2$}]$^-$ (m/z=460), and [Na$_2$Ti$_2$Cl$_8${OCH(CH$_2$)$_2$}]$^-$ (m/z=460), and [Na$_2$Ti$_2$Cl$_8${OCH(CH$_2$)$_2$}$_2$]$^-$ (m/z=540). Anal. Calcd. for C$_{58}$H$_{102}$Cl$_4$N$_8$Na$_2$O$_4$Ti: C, 57.52; H, 8.49; N, 9.25. Found: C, 57.65; H, 8.84; N, 9.44.

[Na(THF)]$_2$[k$^1$-bdmpzp)$_2$TiCl$_4$] (2b) (formula 19). To a diethyl ether (100 mL) suspension of sodium hydride (0.097 g, 4.04 mmol) was added 1,3-bis(3,5-dimethylpyrazol-1-yl)propan-2-ol (1.00 g, 4.03 mmol). The reaction mixture was heated at reflux for 2 h then cooled to room temperature and the suspension was transferred into an addition funnel. The suspension was added dropwise to a cold (0° C.) solution of TiCl$_4$ (0.38 g, 2.01 mmol) in diethyl ether (50 mL). After the addition was complete, the reaction was stirred for 1 h at 0° C. then allowed to warm gradually to ambient temperature and let stir overnight. The suspension was concentrated to dryness and the residue was exhaustively extracted with THF (~100 mL). The solvent was removed under reduced pressure and the pale yellow solid was dried under vacuum. Yield: 0.75 g, 50.1%. $^1$H (CDCl$_3$) d: 1.80 (m, 4H, THF), 2.37 (br s, 24H, CH$_3$), 3.70 (m, 4H, THF), 4.20-5.43 (br overlapping m, 10H, CH$_2$, CH), 5.93 (br s, 4H, pyz-4). Compound 2b typically co-crystallizes with two THF molecules, which can be removed to different extents under vacuum: $^1$H (CDCl$_3$, 50° C.) δ: 1.80 (m, 4H, THF), 2.28 (br s, 12H, CH$_3$), 2.42 (br s, 12H, CH$_3$), 3.70 (m, 4H, THF), 4.40-5.30 (br overlapping m, 10H, CH$_2$, CH), 5.94 (s, 4H, pyz-4). $^{13}$C (CH$_3$CN) δ: 11.8 (CH$_3$), 26.2 (THF), 51.5 (OCH(CH$_2$-pyz)$_2$), 68.4 (THF), 108.3 (OCH(CH$_2$-pyz)$_2$), 147.1 (br s). Anal. Calcd. for C$_{34}$H$_{54}$Cl$_4$N$_8$Na$_2$O$_4$Ti: C, 46.70; H, 6.22; N, 12.81. Found: C, 46.49; H, 5.90; N, 14.33. EI-MS (m/z): 577 [(bdmpzp)$_2$TiCl]$^+$; LDI-TOF MS (negative ion mode, m/z): [Ti$_2$Cl$_4${OCH(CH$_2$)$_2$}]$^-$ (m/z=295), [NaTi$_2$Cl$_7${OCH (CH$_2$)$_2$}]$^-$ (m/z=423) and [Na$_2$Ti$_2$Cl$_8${OCH(CH$_2$)$_2$}$_2$]$^-$ (m/z=540). Anal. Calcd. for C$_{58}$H$_{102}$Cl$_4$N$_8$Na$_2$O$_4$Ti: C, 57.52; H, 8.49; N, 9.25. Found: C, 57.65; H, 8.84; N, 9.44.

(Formula 19)

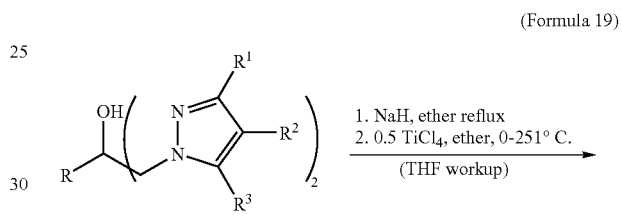

R = R$^2$ = H, R$^1$ = R$^3$ = Bu$^t$; (bdbpzp)H
R = R$^2$ = H, R$^1$ = R$^3$ = Me; (bdmpzp)H 1. NaH, ether reflux
2. 0.5 TiCl$_4$, ether, 0-251° C.
(THF workup)

2a. R$^\ddagger$O = bdbpzp
2b. R$^\ddagger$O = bdmpzp

Example 6

[(bdbpzp)TiCl$_3$] (3a) (formula 20). A THF solution of solution of 1,3-bis(3,5-di-tert-butylpyrazol-1-yl)propan-2-ol (0.625 g, 1.50 mmol) and triethylamine (0.152 g, 1.50 mmol) was added dropwise (over a period of 15 min) into a THF solution (20 mL) of TiCl$_4$(THF)$_2$ (0.500 g, 1.50 mmol) at room temperature. The reaction mixture was stirred for 1 hour and then filtered. The filtrate was concentrated to dryness under reduced pressure and the resulting solid was dried under vacuum for 4 h. Yield: 0.786 g.

[(bdmpzp)TiCl$_3$] (3b) (formula 20). A THF solution of solution of 1,3-bis(3,5-dimethylbutylpyrazol-1-yl)propan-2-ol (0.371 g, 1.50 mmol) and triethylamine (0.152 g, 1.50 mmol) was added dropwise (over a period of 15 min) into a THF solution (20 mL) of TiCl$_4$(THF)$_2$ (0.500 g, 1.50 mmol) at room temperature. The reaction mixture was stirred for 1 hour and then filtered. The filtrate was concentrated to dryness under reduced pressure and the resulting solid was dried under vacuum for 4 h. Yield: 0.488 g.

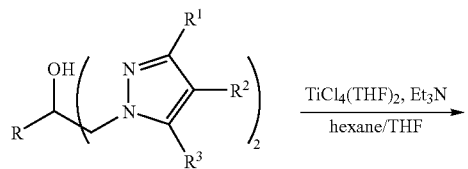

(Formula 20)

R = R² = H, R¹ = R³ = Buᵗ; (bdbpzp)H
R = R² = H, R¹ = R³ = Me; (bdmpzp)H

[(R‡O)TiCl₃]

3a. R‡O = bdbpzp
3b. R‡O = bdmpzp

[(bdmpzp)Ti(CH₂Ph)₃] (3'b) (formula 21). A diethyl ether solution of 1,3-bis(3,5-dimethylpyrazol-1-yl)propan-2-ol (0.183 g, 0.735 mmol) was added dropwise (over a period of 15 min) into a solution of Ti(CH₂Ph)₄ (0.303 g, 0.735 mmol) in diethyl ether (20 mL) at −78° C. The resulting red solution was stirred for an additional 30 minutes and the solvent was removed under reduced pressure while keeping the solution cold (≦0° C.). The red solid was dried under vacuum for 4 h and used without further purification. Yield: 0.386 g, 92%. ¹H ($C_6D_6$): δ 1.74 (s, 6H, pz-CH₃), 2.18 (s, 6H, pz-CH₃), 3.14 (dd, J=14.4, 6.2 Hz, 2H, CH₂), 3.49 (dd, J=14.4, 4.0 Hz, 2H, CH₂), 3.54 (overlapping s, 6H, CH₂Ph), 4.39 (m, 1H, CH), 5.49 (s, 2H, pyz-4), 6.60-7.12 (m, 15H, arom. H).

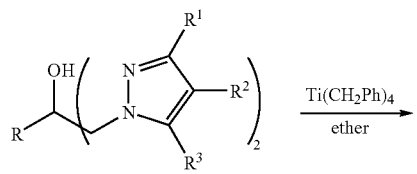

(Formula 21)

R = R² = H, R¹ = R³ = Me; (bdmpzp)H

[(R‡O)Ti(CH₂Ph)₃]

3'b. R‡O = bdmpzp

THF solution (20 mL) of TiCl₄(THF)₂ (0.500 g, 1.50 mmol) at room temperature. The reaction mixture was stirred for 1 hour and then filtered. The filtrate was concentrated to dryness under reduced pressure and the resulting solid was dried under vacuum for 4 h. Yield: 0.463 g.

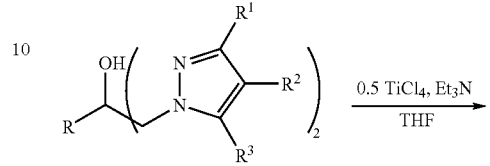

(Formula 22)

R = R² = H, R¹ = R³ = Buᵗ; (bdbpzp)H
R = R² = H, R¹ = R³ = Me; (bdmpzp)H

[(R‡O)₂TiCl₂]

4a. R‡O = bdbpzp
4b. R‡O = bdmpzp

[(bdmpzp)₂Ti(CH₂Ph)₂] (4'b) (formula 23). A diethyl ether solution of 1,3-bis(3,5-dimethylpyrazol-1-yl)propan-2-ol (0.092 g, 0.224 mmol) was added dropwise (over a period of 15 min) into a solution of Ti(CH₂Ph)₄ (0.111 g, 0.448 mmol) in diethyl ether (20 mL) at room temperature. The resulting dark red solution was stirred for an additional 15 minutes and the solvent was removed under reduced pressure while keeping the solution cold (≦0° C.). The red solid was dried under vacuum for 4 h.

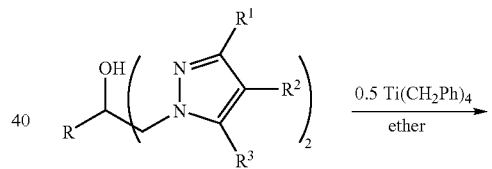

(Formula 23)

R = R² = H, R¹ = R³ = Me; (bdmpzp)H

[(R‡O)₂Ti(CH₂Ph)₂]

4'b. R‡O = bdmpzp

Example 7

[(bdbpzp)₂TiCl₂] (4a) (formula 22). A THF solution of solution of 1,3-bis(3,5-di-tert-butylpyrazol-1-yl)propan-2-ol (1.25 g, 3.00 mmol) and triethylamine (0.304 g, 3.00 mmol) was added dropwise (over a period of 15 min) into a THF solution (20 mL) of TiCl₄(THF)₂ (0.500 g, 1.50 mmol) at room temperature. The reaction mixture was stirred for 1 hour and then filtered. The filtrate was concentrated to dryness under reduced pressure and the resulting solid was dried under vacuum for 4 h. Yield: 1.29 g.

[(bdmpzp)₂TiCl₂] (4b) (formula 22). A THF solution of solution of 1,3-bis(3,5-dimethylbutylpyrazol-1-yl)propan-2-ol (0.742 g, 3.00 mmol) and triethylamine (0.304 g, 3.00 mmol) was added dropwise (over a period of 15 min) into a

Example 8

[(Pr^i₂-admpzp)Ti(OPri)₃] (5a) (formula 24). Into a pentane (20 mL) solution of Ti(OPr^i)₃Cl (0.500 g, 1.92 mmol) was added dropwise a pentane (20 mL) solution of 1-diisopropylamino-3-(3,5-dimethyl-pyrazol-1-yl)-propan-2-ol {(Pr^i₂-admpzp)H, 0.490 g, 1.92 mmol} and NEt₃ (0.194 g, 1.92 mmol). The reaction mixture was let stir for 2 h at room temperature, during which time [HNEt₃]Cl precipitated. After filtering off the precipitate, the yellow filtrate was evaporated under reduced pressure to give 5a as a yellow oily liquid. Yield 0.917 g, 96%.

[(Bn₂-admpzp)Ti(OPri)₃] (5b) (formula 24). Into a pentane (40 mL) solution of Ti(OPr^i)₃Cl (0.500 g, 1.92 mmol) was added dropwise a pentane (20 mL) solution of 1-dibenzylamino-3-(3,5-dimethyl-pyrazol-1-yl)-propan-2-ol {(Bn$_2$-admpzp)H, 0.670 g, 1.92 mmol} and NEt$_3$ (0.194 g, 1.92 mmol). The reaction mixture was let stir for 2 h at room temperature, during which time [HNEt$_3$]Cl precipitated. After filtering off the precipitate, the yellow filtrate was evaporated under reduced pressure to give 5b as a yellow oily liquid. Yield 1.07 g, 97%.

Novel Isolated Compounds

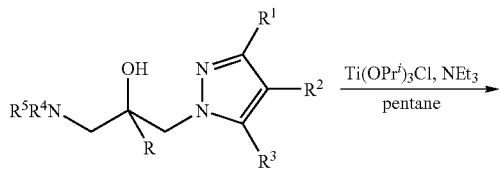

(Formula 24)

R = R$^2$ = H, R$^1$ = R$^3$ = Me, R$^4$ = R$^5$ = Pr$^i$: (Pr$^i{}_2$-admpzp)H
R = R$^2$ = H, R$^1$ = R$^3$ = Me, R$^4$ = R$^5$ = CH$_2$Ph: (Bn$_2$-admpzp)H

[(RR'-admpzp)Ti(OPr$^i$)$_3$]

5a. R$^4$ = R$^5$ = Pr$^i$
5b. R$^4$ = R$^5$ = CH$_2$Ph

Example 9

[(Pr$^i{}_2$-admpzp)$_2$Ti(OPri)$_2$] (6a) (formula 25). Into a pentane (20 mL) solution of Ti(OPr$^i$)$_3$Cl (0.500 g, 1.92 mmol) was added dropwise a pentane (20 mL) solution of 1-diisopropylamino-3-(3,5-dimethyl-pyrazol-1-yl)-propan-2-ol {(Pr$^i{}_2$-admpzp)H, 0.490 g, 1.92 mmol} and NEt$_3$ (0.194 g, 1.92 mmol). Next, another equivalent of (Pr$^i{}_2$-admpzp)H (0.490 g, 1.92 mmol) in pentane (20 mL) was slowly added. The reaction mixture was let stir for 2 h at room temperature, during which time [HNEt$_3$]Cl precipitated. After filtering off the precipitate, the yellow filtrate was evaporated under reduced pressure to give 6a as a yellow oily liquid. This product could be obtained as a colorless oil following dissolution in pentane, filtration through a plug of dry activated carbon, and evaporation of the solvent. Yield 1.24 g, 96%. $^1$H (C$_6$D$_6$) δ: 5.68 (br s, 2H, pyz-4), 5.12-4.46 (br m, 4H, Ti—OCH—), 4.44-4.10 (m, 2H, H$_A$ of —CH$_2$pyz), 3.82-3.54, (m, 2H, H$_B$ of —CH$_2$pyz), 3.07-2.78 (br m, 4H, N(CHMe$_2$)$_2$) 2.93-2.70 {m, 2H, (H$_A$ of —CH$_2$NPr$^i{}_2$}, 2.63-2.38 (m, 6H, CH$_3$ at pyz-3), 2.38-2.25 (m, 2H, H$_B$ of —CH$_2$NPr$^i{}_2$), 2.20-1.87 {m, 6H, (CH$_3$ at pyz-5)}, 1.45-1.24 (m, 12H, Ti—OCHMe$_2$), 1.07-0.72 (br m, 24H, {N(CHMe$_2$)$_2$}. $^{13}$C (C$_6$D$_6$) δ: 147.8 (pyz-3), 147.3 (pyz-3), 139.2 (pyz-5), 105.0 (pyz-4), 81.7 (Ti—OCH—), 80.8 (Ti—OCH—), 77.0 (Ti—OCH—), 52.7 (—CH$_2$pyz), 50.5 (CH$_2$NPr$^i{}_2$), 48.6 (CH$_2$NPr$^i{}_2$), 26.7 (Ti—OCHMe$_2$), 22.3 {N(CHMe$_2$)$^2$}, 19.9 {N(CHMe$_2$)$_2$}, 14.2 (CH$_3$ at pyz-3), 11.0 (CH$_3$ at pyz-5). IR (neat, cm$^{-1}$): 2965, 2928, 2867, 2617, 1553, 1464, 1425, 1385, 1362, 1324, 1260, 1207, 1123, 1045, 987, 930, 886, 809, 775, 738, 696, 632. Anal. Calcd. for C$_{34}$H$_{66}$N$_6$O$_4$Ti: C, 60.88; H, 9.92; N, 12.53. Found: C, 61.11; H, 9.81; N, 12.63.

[(Bn$_2$-admpzp)$_2$Ti(OPri)$_2$] (6b) (formula 25). Into a pentane (20 mL) solution of Ti(OPr$^i$)$_3$Cl (0.500 g, 1.92 mmol) was slowly added (dropwise) a pentane (40 mL) solution of 1-dibenzylamino-3-(3,5-dimethyl-pyrazol-1-yl)-propan-2-ol {(Bn$_2$-admpzp)H, 0.670 g, 1.92 mmol} and NEt$_3$ (0.194 g, 1.92 mmol). Next, another equivalent of (Bn$_2$-admpzp)H (0.670 g, 1.92 mmol) in pentane (40 mL) was slowly added. The reaction mixture was let stir for 2 h at room temperature, during which time [HNEt$_3$]Cl precipitated. After the precipitate was filtered off, the yellow filtrate was cooled at −30° C. overnight. The bottom layer of the resulting biphasic mixture was collected and dried under vacuum for 4 h to give 6b as a viscous yellow liquid. A colorless oil could be obtained via dissolution in pentane, filtration through a plug of dry activated carbon, and evaporation of the solvent. Yield: 1.56 g. 94%. $^1$H (C$_6$D$_6$) δ: 7.50-6.98 (m, 20H, {PhCH$_2$)$_2$N}, 5.55 (br s, 2H, pyz-4), 4.95-4.60 (br m, 4H, Ti—OCH—), 4.22-4.00 (m, 2H, H$_A$ of CH$_2$pyz), 3.93-3.67 (m, 4H, H$_A$ of (PhCH$_2$)$_2$N), 3.67-3.26 (m, 2H, H$_B$ of CH$_2$pyz), 3.47-3.26 (m, 4H, H$_B$ of (PhCH$_2$)$_2$N), 2.81-2.50 (br m, 4H, —CH$_2$NBn$_2$), 2.47-2.08 (m, 6H, CH$_3$ at pyz-3), 2.06-1.67 (m, 6H, (CH$_3$ at pyz-5), 1.45-0.80 (br m, 12H, Ti—OCHMe$_2$). $^{13}$C (C$_6$D$_6$) δ: 147.8 (pyz-3), 140.1 (pyz-5), 139.2, 129.4, 128.4, 127.1 {(PhCH$_2$)$_2$N}, 105.0 (pyz-4), 79.4 (Ti—OCH—), 77.4 (Ti—OCH—), 59.4 {(PhCH$_2$)$_2$N}, 59.0 (—CH$_2$NBn$_2$), 52.8 (CH$_2$pyz), 26.5 (Ti—OCHMe$_2$), 14.2 (CH$_3$ at pyz-3), 11.1 (CH$_3$ at pyz-5). IR (neat, cm$^{-1}$): 3084, 3061, 3027, 2963, 2853, 2792, 2714, 2617, 1948, 1877, 1809, 1754, 1602, 1585, 1553, 1494, 1454, 1373, 1240, 1097, 1018, 933, 847, 780, 747, 698. Anal. Calcd. for C$_{50}$H$_{66}$N$_6$O$_4$Ti: C, 69.59; H, 7.71; N, 9.74. Found: C, 69.65; H, 7.91; N, 9.80.

[(Bu$^t$Bn-admpzp)$_2$Ti(OPri)$_2$] (6c) (formula 25). Into a pentane (20 mL) solution of Ti(OPr$^i$)$_3$Cl (0.500 g, 1.92 mmol) was slowly added (dropwise) a pentane (20 mL) solution of 1-(benzyl-tert-butyl-amino)-3-(3,5-dimethyl-pyrazol-1-yl)-propan-2-ol {(Bu$^t$Bn-admpzp)H, 0.610 g, 1.92 mmol} and NEt$_3$ (0.194 g, 1.92 mmol). Next, another equivalent of (Bu$^t$Bn-admpzp)H (0.610 g, 1.92 mmol) in pentane (20 mL) was slowly added. The reaction mixture was let stir for 2 h at room temperature, during which time [HNEt$_3$]Cl precipitated. After the precipitate was filtered off, the filtrate was concentrated under reduced pressure to ~20 mL and cooled at −30° C. overnight. The resulting yellowish-white crystals were collected, recrystallized from hot pentane by cooling a saturated solution at −30° C. for several days, and then dried under vacuum to give 6c. Yield: 1.13 g. 74%. $^1$H (C$_6$D$_6$) δ: 7.62-6.99 (m, 10H, Bu$^t$(PhCH$_2$)N), 5.60 (br m, 2H, pyz-4), 5.16-4.32 (br m, 4H, Ti—OCH—), 4.12-3.82 (m, 2H, H$_A$ of CH$_2$pyz), 3.83-3.50, (m, 4H, Bu$^t$(PhCH$_2$)N), 3.50-3.31 (m, 2H, H$_B$ of CH$_2$pyz), 3.05-2.64 (br m, 4H, —CH$_2$NBnBu$^t$), 2.65-2.15 (m, 6H, CH$_3$ at pyz-3), 2.14-1.68 (m, 6H, CH$_3$ at pyz-5), 1.51-1.17 (m, 12H, Ti—OCHMe$_2$), 1.15-0.85 (m, 18H, Bu$^t$). $^{13}$C (C$_6$D$_6$) δ: 148.0 (pyz-3), 144.1 (Bu$^t$(PhCH$_2$)N), 139.0 (pyz-5), 128.4 (Bu$^t$(PhCH$_2$)N), 127.1 (Bu$^t$(PhCH$_2$)N), 126.5 (Bu$^t$(PhCH$_2$)N), 105.0 (pyz-4), 80.7 (Ti—OCH—), 76.9 (Ti—OCH—), 57.0 (Bn(Me$_3$C)N), 56.1 (—CH$_2$NBnBu$^t$), 55.5 (Bu$^t$(PhCH$_2$)N), 52.3 (CH$_2$pyz), 27.3 (Ti—OCHMe$_2$), 26.5 (Bn(CH$_3$)$_3$CN), 14.3 (CH$_3$ at pyz-3), 11.1 (CH$_3$ at pyz-5). IR (Nujol, cm$^{-1}$): 1551, 1465, 1367, 1323, 1296, 1201, 1160, 1135, 1092, 989, 931, 843, 734, 699. Anal. Calcd. for C$_{44}$H$_{70}$N$_6$O$_4$Ti: C, 66.48; H, 8.88; N, 10.57. Found: C, 66.33; H, 8.75; N, 10.69.

Novel Isolated Compounds

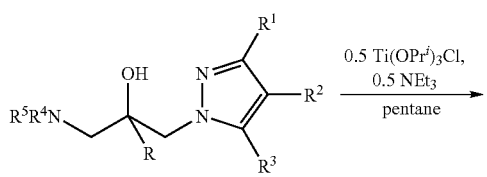

R = R² = H, R¹ = R³ = Me, R⁴ = R⁵ = Pr$^i$: (Pr$^i_2$-admpzp)H
R = R² = H, R¹ = R³ = Me, R⁴ = R⁵ = CH₂Ph: (Bn₂-admpzp)H
R = R² = H, R¹ = R³ = Me, R⁴ = Bu$^t$, R⁵ = CH₂Ph: (Bu$^t$Bn-admpzp)H

[(RR'-admpzp)₂Ti(OPr$^i$)₂]

6a. R⁴ = R⁵ = Pr$^i$
6b. R⁴ = R⁵ = CH₂Ph
6c. R⁴ = Bu$^t$, R⁵ = CH₂PH

Example 10

[(Phdmpzp)Ti(CH₂Ph)₃] (formula 26). A diethyl ether solution of 1-phenyl-3-(3,5-dimethyl-pyrazol-1-yl)-propan-2-ol {(Phdmpzp)H, 1 mmol} is added dropwise into a solution of Ti(CH₂Ph)₄ (1 mmol) in diethyl ether at low temperature (−78° C.). After stirring the reaction mixture for an additional 15-120 minutes, the solvent is removed under reduced pressure and the residue is then dried under vacuum.

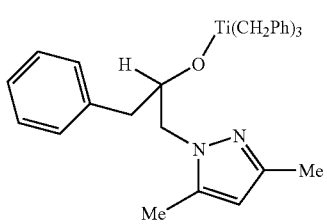
(Formula 26)

[(Phdmpzb)Ti(CH₂Ph)₃] (formula 27). This compound will be prepared in a manner similar to that described above for [(Phdmpzp)Ti(CH₂Ph)₃], except 4-phenyl-1-(3,5-dimethyl-pyrazol-1-yl)-butan-2-ol ((Phdmpzb)H) will be used.

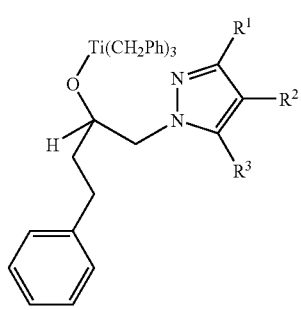
(formula 27)

where R¹, R² and R³=hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen.

Example 11

[(Phdmpzp)₂Ti(CH₂Ph)₂] (formula 28). A diethyl ether solution of 1-phenyl-3-(3,5-dimethyl-pyrazol-1-yl)-propan-2-ol {(Phdmpzp)H, 1 mmol} is added dropwise into a solution of Ti(CH₂Ph)₄ (0.5 mmol) in diethyl ether at ambient or low temperature (−78° C.). After stirring the reaction mixture for an additional 15-120 minutes, the solvent is removed under reduced pressure and the residue is then dried under vacuum.

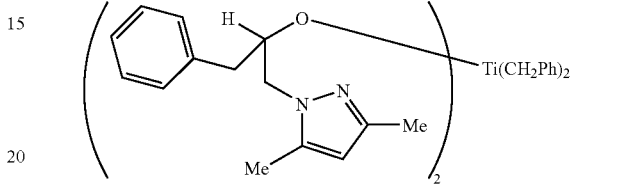
(Formula 28)

[(Phdmpzb)₂Ti(CH₂Ph)₂] (formula 29). This compound will be prepared in a manner to that described above for [(Phdmpzp)₂Ti(CH₂Ph)₂], except 4-phenyl-1-(3,5-dimethyl-pyrazol-1-yl)-butan-2-ol ((Phdmpzb)H) will be used.

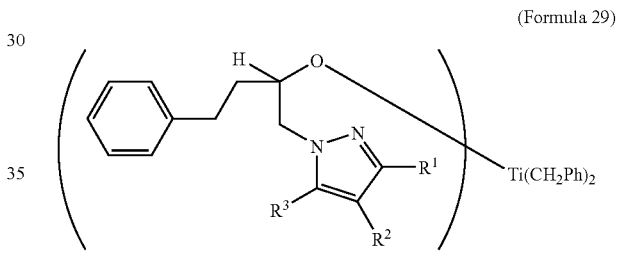
(Formula 29)

where R¹, R² and R³=hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen.

Example 12

[{PhCH₂C(Pr$^i$)₂O}Ti(NMe₂)₃] (9a). A hexane solution (5 mL) of PhCH₂C(Pr$^i$)₂OH (0.206 g, 1 mmol) was added dropwise (over 20 minutes) into a hexane solution (5 mL) of Ti(NMe₂)₄ (0.224 g, 1 mmol) at room temperature. After stirring for 1 h, the reaction mixture was stripped to dryness under reduced pressure. The resulting yellow oil was dried under vacuum for 3 hours. Yield: 0.35 g, 91%. $^1$H NMR (C₆D₆) δ: 7.41 (d, 2H, arom CH), 7.21 (m, 3H, arom CH), 3.12 (s, 18H, N(CH₃)₂—CH₃), 2.93 (s, 2H, PhCH₂), 2.09 (hep, 2H, CH(CH₃)₂), 1.13 (d, 6H, CH(CH₃)₂), 1.01 (d, 6H, CH(CH₃)₂). $^{13}$C NMR (C₆D₆) δ: 139.9 (C₆H₅CH₂), 131.4 (C₆H₅CH₂), 128.4 (C₆H₅CH₂), 126.1 (C₆H₅CH₂), 91.0 (C₆H₅CH₂CO), 45.3 (N(CH₃)₂), 41.4 (C₆H₅CH₂), 35.5 (CH(CH₃)₂), 18.8 (CH(CH₃)₂), 18.5 (CH(CH₃)₂). Anal. Calcd. for C₂₀H₃₉N₃OTi: C, 62.33; H, 10.20; N, 10.90. Found: C, 62.18; H, 10.09; N, 10.73.

[{PhCH₂C(Pr$^i$)₂O}Ti(NMe₂)Cl₂] (9b). Into an ether solution (5 mL) of [{PhCH₂C(Pr$^i$)₂O}Ti(NMe₂)₃] (9a, 0.385 g, 1 mmol) was added an ether solution (8 mL) of Me₃SiCl (0.654 g, 6 mmol) at room temperature. After stirring for 18 h, the resulting orange-yellow reaction mixture was stripped to dryness under reduced pressure. The resulting dark red oil was dried under vacuum for 3 hours. Yield: 0.31 g, 67%. $^1$H NMR (CDCl$_3$) δ: 7.34 (d, 2H, arom CH), 7.26 (m, 3H, arom CH), 3.46 (s, 6H, N(CH$_3$)$_2$), 3.14 (s, 2H, PhCH$_2$), 2.37 (hep, 2H, CH(CH$_3$)$_2$), 1.21 (d, 6H, CH(CH$_3$)$_2$), 1.06 (d, 6H, CH(CH$_3$)$_2$). $^{13}$C-NMR (CDCl$_3$) δ: 137.3 (C$_6$H$_5$CH$_2$), 131.2 (C$_6$H$_5$CH$_2$), 128.5 (C$_6$H$_5$CH$_2$), 128.9 (C$_6$H$_5$CH$_2$), 107.2 (C$_6$H$_5$CH$_2$CO), 48.7 (N(CH$_3$)$_2$), 40.0 (C$_6$H$_5$CH$_2$), 35.6 (CH(CH$_3$)$_2$), 19.0 (CH(CH$_3$)$_2$), 18.6 (CH(CH$_3$)$_2$). Anal. Calcd. for C$_{16}$H$_{27}$Cl$_2$NOTi: C, 52.2; H, 7.39; N, 3.80. Found: C, 51.84; H, 7.20; N, 4.06.

Novel Isolated Compounds

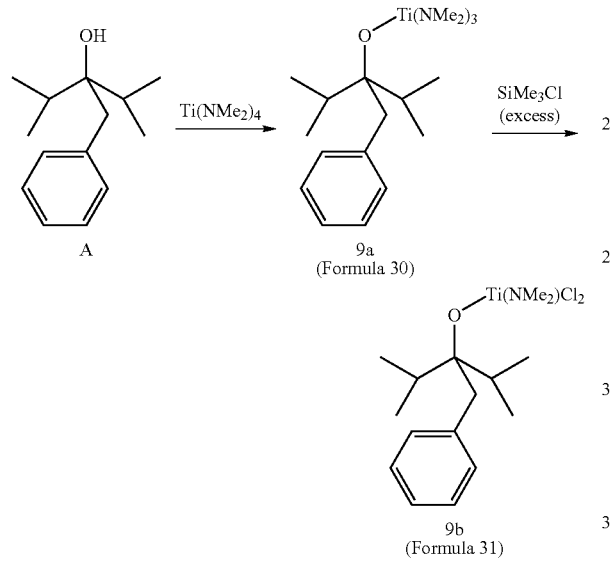

9a (Formula 30)

9b (Formula 31)

A: prepared as described by Pettersson, Ingrid; Berg, Ulf, Conformational analysis of _-alkyl-_,_-diisopropylstyrenes. A dymanic proton nuclear magnetic resonance spectroscopic and molecular mechanics investigation. Journal of the Chemical Society, Perkin Transaction 2: Physical Organic Chemistry (1972-1999) (1985), (9), 1365-75.

(CDCl$_3$) δ: 7.26 (m, 2H, arom CH), 7.09 (m, 3H, arom CH), 3.10 (s, 2H, PhCH$_2$), 2.20 (hep, 2H, CH(CH$_3$)$_2$), 1.14 (d, 6H, CH(CH$_3$)$_2$), 0.87 (d, 6H, CH(CH$_3$)$_2$). $^{13}$C-NMR (CDCl$_3$) δ: 136.9 (C$_6$H$_5$CH$_2$), 130.6 (C$_6$H$_5$CH$_2$), 128.2 (C$_6$H$_5$CH$_2$), 126.5 (C$_6$H$_5$CH$_2$), 106.6 (C$_6$H$_5$CH$_2$CO), 39.8 (C$_6$H$_5$CH$_2$), 35.2 (CH(CH$_3$)$_2$), 18.1 (CH(CH$_3$)$_2$), 18.0 (CH(CH$_3$)$_2$). Anal. Calcd for C$_{28}$H$_{42}$Cl$_2$O$_2$Ti: C, 63.52; H, 8.00. Found: C, 63.48; H, 7.99.

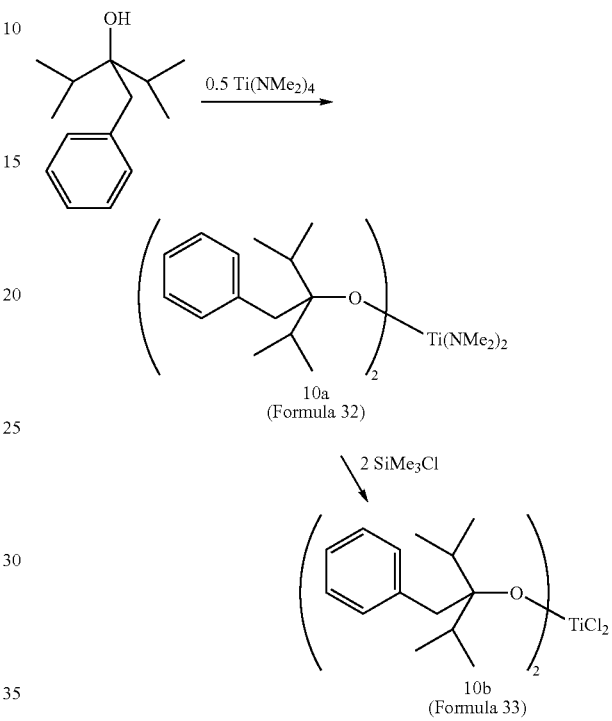

10a (Formula 32)

10b (Formula 33)

Example 14

Typical Procedure for Ethylene Polymerization. Toluene was charged into a 600 mL Parr reactor equipped with a mechanical stirrer. Next, a 10% by weight toluene solution of methylalumoxane (MAO, ≧1000 equivalents) was added. The precatalyst (typically, 0.2-20 μmol) was charged into an isolated catalyst addition chamber in the reactor. The reactor was sealed under N$_2$ atmosphere and then charged with ethylene to 7 bar pressure and maintained at the desired temperature for 20 min. The catalyst was charged into the reaction mixture using a stream of ethylene at 10 bar pressure and the pressure inside the chamber was maintained at 10 bar pressure throughout the course of the reaction. After the required time, the reactor was vented, and the reaction quenched with ethanol (30 mL) and then 1 M HCl solution (30 mL). The resulting suspension was vigorously stirred until both layers were colorless and clearly separated (~10 min). Polyethylene was filtered off, washed with 1M HCl, and ethanol then dried at in a vacuum oven at 60° C. for 24-48 h.

Example 13

[{PhCH$_2$C(Pr$^i$)$_2$O}$_2$Ti(NMe$_2$)$_2$] (10a). A hexane solution (10 mL) of PhCH$_2$C(Pr$^i$)$_2$OH (0.412 g, 2 mmol) was added dropwise (over 20 minutes) into a hexane solution (5 mL) of Ti(NMe$_2$)$_4$ (0.224 g, 1 mmol) at room temperature. After stirring for 1 h, the reaction mixture was stripped to dryness under reduced pressure. The resulting yellow waxy residue was dried under vacuum for 3 hours. Yield: 0.50 g, 91.2%. $^1$H-NMR (C$_6$D$_6$) δ: 7.45 (d, 4H, arom CH), 7.20 (m, 6H, arom CH), 3.16 (s, 12H, N(CH$_3$)$_2$—CH$_3$), 3.08 (s, 4H, PhCH$_2$), 2.18 (hep, 4H, CH(CH$_3$)$_2$), 1.21 (d, 12H, CH(CH$_3$)$_2$), 1.00 (d, 12H, CH(CH$_3$)$_2$). $^{13}$C NMR (C$_6$D$_6$): δ 139.9 (C$_6$H$_5$CH$_2$), 131.3 (C$_6$H$_5$CH$_2$), 128.5 (C$_6$H$_5$CH$_2$), 126.4 (C$_6$H$_5$CH$_2$), 92.3 (C$_6$H$_5$CH$_2$CO), 46.5 (N(CH$_3$)$_2$), 42.0 (C$_6$H$_5$CH$_2$), 35.4 (CH(CH$_3$)$_2$), 18.5 (CH(CH$_3$)$_2$), 18.4 (CH(CH$_3$)$_2$). Anal. Calcd. for C$_{32}$H$_{54}$N$_2$O$_2$Ti: C, 70.31; H. 9.96; N, 5.12. Found: C, 70.11; H, 9.90; N, 5.33.

[{PhCH$_2$C(Pr$^i$)$_2$O}$_2$TiCl$_2$] (10b). Into an ether solution (5 mL) of [{PhCH$_2$C(Pr$^i$)$_2$O}$_2$Ti(NMe$_2$)$_2$] (10a, 0.547 g, 1 mmol) was added an ether solution (10 mL) of Me$_3$SiCl (0.432 g, 4 mmol) at room temperature. After stirring for 18 h, the light-yellow reaction mixture was stripped to dryness under reduced pressure. The resulting light-yellow oil was dried under vacuum for 3 hours. Yield: 0.33 g, 63%. $^1$H NMR Example 15

Comparative Test Data

Table 1 (below) presents comparative data illustrating the catalytic activity resulting from use of some of the claimed titanium-containing precatalysts in the polymerization reaction of ethylene in the manner set forth in example 14.

TABLE 1

Summary of Ethylene Polymerization Results conditions unless otherwise stated:

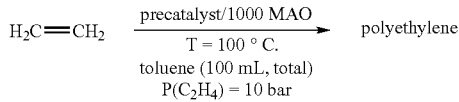

$$H_2C=CH_2 \xrightarrow[\substack{T = 100\,°C \\ \text{toluene (100 mL, total)} \\ P(C_2H_4) = 10 \text{ bar}}]{\text{precatalyst/1000 MAO}} \text{polyethylene}$$

reaction vessel = 600 mL stainless steel parr reactor

| # | precatalyst | [Ti] (M) | T (°C.) | t (min) | activity [g PE/(mol Ti·h·bar)] | $10^{-3}M_w{}^g$ | $M_w/M_n{}^g$ |
|---|---|---|---|---|---|---|---|
| 1 | [{PhCH$_2$C(Pr$^i$)$_2$O}Ti(NMe$_2$)$_3$] (9a).$^a$ | 2 × 10$^{-4}$ | 100 | 15 | 92640 | 153297 | 1.5 |
| 2 | 9a$^a$ | 2 × 10$^{-4}$ | 100 | 30 | 90700 | 169392 | 1.5 |
| 3 | 9a$^a$ | 2 × 10$^{-4}$ | 100 | 45 | 110073 | 151005 | 1.5 |
| 4 | 9a$^{a,b}$ | 1 × 10$^{-5}$ | 100 | 30 | 157680 | | |
| 5 | 9a$^{a,c}$ | 2 × 10$^{-6}$ | 100 | 30 | 411000 | | |
| 6 | Na[(κ$^1$-bdmpzp)TiCl$_4$(THF)] (1b)$^a$ | 1 × 10$^{-5}$ | 100 | 30 | 104200 | 107 | 1.6 |
| 7 | 1b$^a$ | 1.8 × 10$^{-4}$ | 100 | 30 | 10000 | — | — |
| 8 | Na[(κ$^1$-bdbpzp)TiCl$_4$(THF)] (1a)$^a$ | 1.8 × 10$^{-4}$ | 100 | 30 | 16600 | 97 | 1.7 |
| 9 | 1a$^a$ | 1 × 10$^{-5}$ | 100 | 5 | 168000 | | |
| 10 | [Na(THF)]$_2$[(κ$^1$-bdmpzp)$_2$TiCl$_4$] (2b)$^a$ | 1 × 10$^{-6}$ | 100 | 30 | 422000 | | |
| 11 | 2b$^a$ | 1 × 10$^{-5}$ | 100 | 30 | 124400 | 105 | 1.7 |
| 12 | 2b$^a$ | 1.8 × 10$^{-4}$ | 100 | 30 | 20000 | 107 | 1.9 |
| 13 | [(dmpzp)Ti(CH$_2$)$_3$] (3'b)$^a$ | 2 × 10$^{-4}$ | 100 | 30 | 28000 | 92 | 1.8 |
| 14 | [(Bu$^t$Bn-admpzp)$_2$Ti(OPr$^i$)$_2$] (6c)$^a$ | 1 × 10$^{-4}$ | 100 | 30 | 19000 | 146 | 2.1 |
| 15 | (bdbpzp)$_2$TiCl$_2$(4a)$^a$ | 1 × 10$^{-5}$ | 100 | 1 | 428400 | | |
| 16 | Cp$_2$TiCl$_2{}^a$ | 1 × 10$^{-5}$ | 100 | 30 | 42000 | | |
| 17 | Cp$_2$TiCl$_2{}^d$ | 2 × 10$^{-5}$ | 50 | 120 | 41000 | | |
| 18 | Cp$_2$ZrCl$_2{}^a$ | 1 × 10$^{-5}$ | 25 | 30 | 1508000 | | |
| 19 | Cp$_2$ZrCl$_2{}^{e,h}$ | 1.25 × 10$^{-5}$ | 60 | 4 | 6300000 | | |
| 20 | Tp$^{MS}$TiCl$_3{}^{e,h}$ | 1.25 × 10$^{-5}$ | 60 | 6 | 4300000 | | 4-15 |
| 21 | [(bdmpza)TiCl$_2${O(CH$_2$)$_4$Cl}]$^{f,i}$ | 2.7 × 10$^{-5}$ | 45 | 30 | 400000 | 350000 | 8.2 |

$^a$polymerizations conditions (unless stated otherwise): 600 mL stainless steel Parr reactor; solvent = toluene (100 mL total); P(C$_2$H$_4$) = 10 bar; 1000 equivalents of MAO (10 wt % total Al in toluene solution).
$^b$6250 equivalents of MAO used.
$^c$31250 equivalents of MAO used.
$^d$2155 equivalents of MAO used; P(C$_2$H$_4$) = 1.31 bar; 100 mL toluene (total); stainless steel Parr reactor.
$^e$P(C$_2$H$_4$) = 4.28 bar; 80 mL toluene (total); glass Fischer-Porter reactor.
$^f$2000 equivalents of MAO used; P(C$_2$H$_4$) = 3.4 bar; solvent = toluene; Buchi autoclave (reactor).
$^g$determined by GPC.
$^h$Murtuza, S.; Casagrande, Jr., O. L.; Jordan, R. F. Organometallics 2002, 21, 1882.
$^i$Otero, A.; Fernández-Baeza, J.; Antiñolo, A.; Carrillo-Hermosilla, F.; Tejeda, J.; Diez-Barra, E.; Lara-Sánchez, A.; Sanchez-Barba, L.; Lopez-Solera, I. Organometallics 2001, 20, 2428.

As shown in Table 1, preliminary study of the ethylene polymerization behavior of titanium precatalysts containing 1,3-bis(pyrazol-1yl)propan-2-olate ligand, such as Na[(bd-mpzp)(THF)TiCl$_4$] (1a), [Na(THF)]$_2$[(bdmpzp)$_2$TiCl$_4$] (2b), and [(bdmpzp)Ti(CH$_2$Ph)$_3$] (3'b), as well as titanium precatalysts containing alkoxide-arene ligand, such as [{PhCH$_2$C(Pr$^i$)$_2$O}Ti(NMe$_2$)$_3$] (9a), demonstrate that they display substantially higher activity than the Cp$_2$TiCl$_2$/MAO system under high temperature solution polymerization conditions (compare entries 1-15 versus 16 and 17). In fact, our titanium precatalysts display activities comparable to (less than an order of magnitude lower than) that reported for the commercially important Cp$_2$ZrCl$_2$/MAO system under similar polymerization conditions (compare entries 1-15 versus 18 and 19). Equally important, GPC analyses of polyethylenes obtained using our catalysts indicate that they possess narrow molecular weight distributions ($M_w/M_n$=1.5-2.1) and molecular weights between ca. 100,000 and 170,000; the molecular weight distributions are generally less than 2, as expected for single-site catalysts. DSC analyses demonstrated that the polyethylenes are essentially linear and show melting points of ca. 135° C. Thus, the activity data for our catalysts is consistent with a stable polymerization profile and modest catalyst decay at 100° C., suggesting that the active catalyst species is stable under these conditions.

The foregoing description of the preferred embodiments of the present invention have been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed is:

1. A method of polymerizing an olefin, comprising:
conducting a polymerization reaction of said olefin in the presence of a catalyst formed by a compound with the formula:

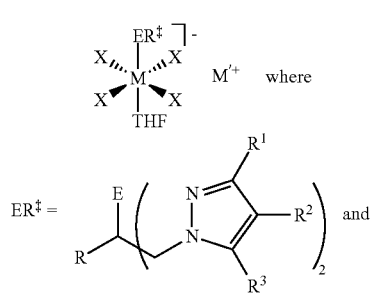

(Formula 4)

M=Ti, Zr or Hf, E=O or S, R, $R^1$, $R^2$ and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, X=halogen, and $M'^+$=an alkali metal ion or any monopositive cation.

2. A method of polymerizing an olefin, comprising:
conducting a polymerization reaction of said olefin in the presence of a catalyst formed by a compound with the formula:

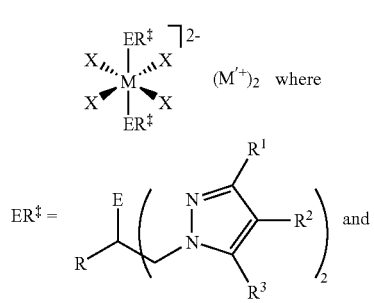

(Formula 5)

M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, X=halogen, and $M'^+$=an alkali metal ion or any monopositive cation; $(M'^+)_2$=any dipositive cation.

3. A method of polymerizing an olefin, comprising:
conducting a polymerization reaction of said olefin in the presence of a catalyst formed by a compound with the formula:

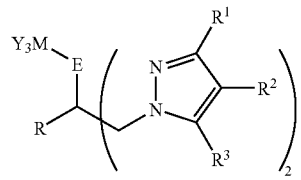

(formula 6)

where M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, and Y=an anionic monodentate ligand.

4. A method of polymerizing an olefin, comprising:
conducting a polymerization reaction of said olefin in the presence of a catalyst formed by a compound with the formula:

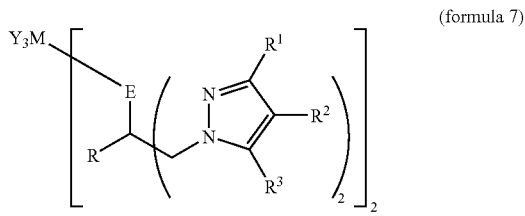

(formula 7)

where M=Ti, Zr or Hf, E=O or S, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, and Y=an anionic monodentate ligand.

5. A method of polymerizing an olefin, comprising:
conducting a polymerization reaction of said olefin in the presence of a catalyst formed by a compound with the formula:

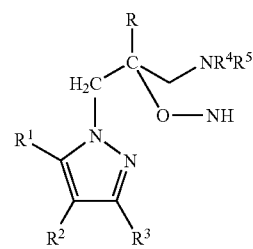

(formula 8)

where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, and Y=an anionic monodentate ligand.

6. A method of polymerizing an olefin, comprising:
conducting a polymerization reaction of said olefin in the presence of a catalyst formed by a compound with the formula:

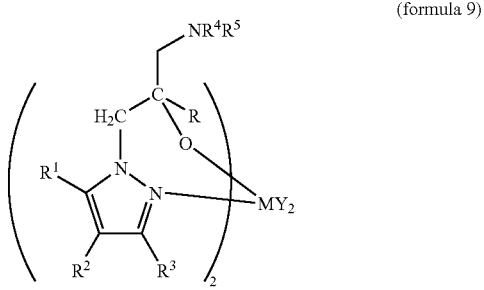

(formula 9)

where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen and Y=an anionic monodentate ligand.

7. A method of polymerizing an olefin, comprising:
conducting a polymerization reaction of said olefin in the presence of a catalyst formed by a compound with the formula:

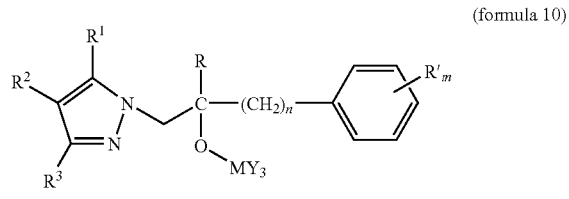

(formula 10)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=an anionic monodentate ligand.

8. A method of polymerizing an olefin, comprising:
conducting a polymerization reaction of said olefin in the presence of a catalyst formed by a compound with the formula:

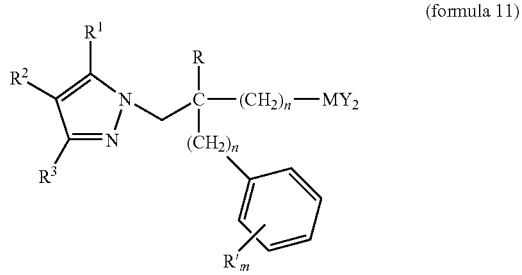

(formula 11)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=an anionic monodentate ligand.

9. A method of polymerizing an olefin, comprising:
conducting a polymerization reaction of said olefin in the presence of a catalyst formed by a compound with the formula:

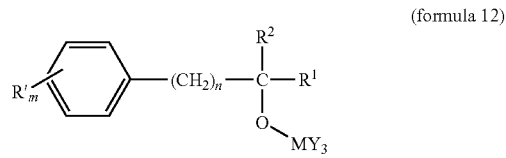

(formula 12)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=anionic monodentate ligand.

10. A method of polymerizing an olefin, comprising:
conducting a polymerization reaction of said olefin in the presence of a catalyst formed by a compound with the formula:

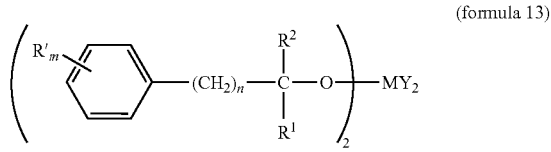

(formula 13)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=anionic monodentate ligand.

11. A method of polymerizing an olefin, comprising:
conducting a polymerization reaction of said olefin in the presence of a catalyst formed by a compound selected from a group consisting of:

(a)

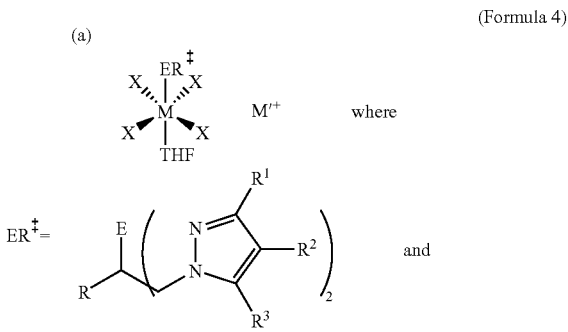

(Formula 4)

M=Ti, Zr or Hf, E=O or S, R, $R^1$, $R^2$ and $R^3$ are independently the same or different and are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, X=halogen, and M'+=an alkali metal ion or any monopositive cation;

(b) (Formula 5)

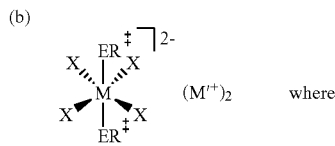

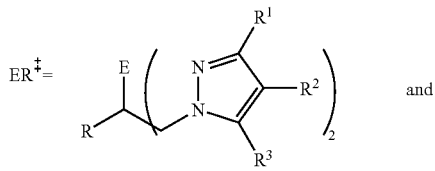

and

M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, X=halogen, and M'+=an alkali metal ion or any monopositive cation; $(M'^+)_2$=any dipositive cation;

(c) (formula 6)

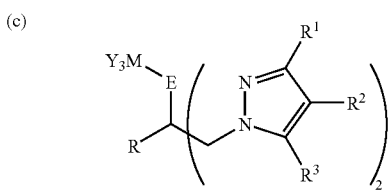

where M=Ti, Zr or Hf, E=O or S, R, $R^1$, $R^2$ and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, and Y=an anionic monodentate ligand;

(d) (formula 7)

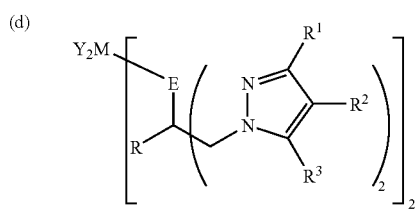

where M=Ti, Zr or Hf, E=O or S, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, and Y=an anionic monodentate ligand;

(e) (formula 8)

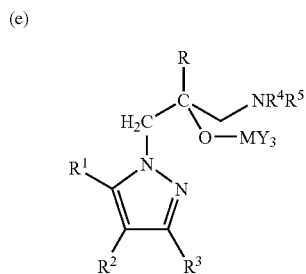

where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, and Y=an anionic monodentate ligand;

(f) (formula 9)

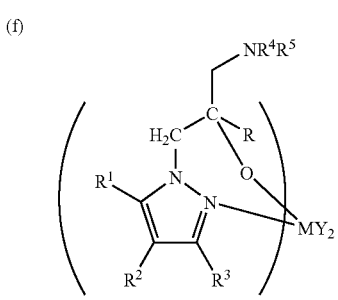

where M=Ti, Zr or Hf, R, $R^1$, $R^2$, $R^3$, $R^4$ and $R^5$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen and Y=an anionic monodentate ligand;

(g) (formula 10)

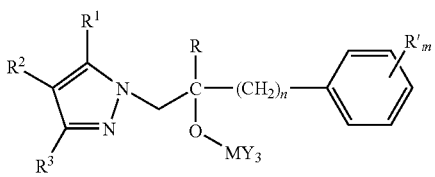

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=an anionic monodentate ligand;

(h)

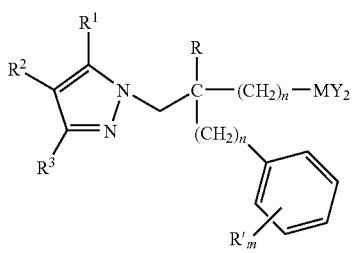

(formula 11)

where M=Ti, Zr or Hf, R, $R^1$, $R^2$, and $R^3$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=an anionic monodentate ligand;

(i)

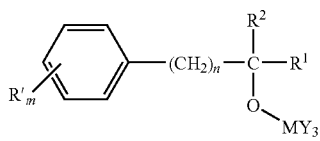

(formula 12)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=anionic monodentate ligand; and (j)

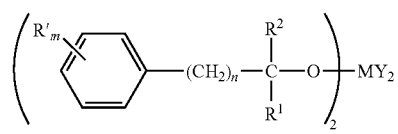

(formula 13)

where M=Ti, Zr or Hf, $R^1$ and $R^2$ are hydrogen, a branched or linear alkyl group, a branched or linear alkenyl group, a branched or linear alkynyl group, a cycloalkyl group, a cycloalkenyl group, an alkoxy group, an aryl group, a silyl group, or a halogen, R'=an aryl group, a silyl group, halogen, an alkoxo group, or amido group, m=0-5, n=1 or 2 and Y=anionic monodentate ligand.

* * * * *

UNITED STATES PATENT AND TRADEMARK OFFICE
CERTIFICATE OF CORRECTION

| | | |
|---|---|---|
| PATENT NO. | : 7,851,570 B2 | Page 1 of 1 |
| APPLICATION NO. | : 11/710174 | |
| DATED | : December 14, 2010 | |
| INVENTOR(S) | : Ladipo et al. | |

It is certified that error appears in the above-identified patent and that said Letters Patent is hereby corrected as shown below:

Claim 5, column 28, line 45, please replace the incorrect formula 8 with the following correct formula 8:

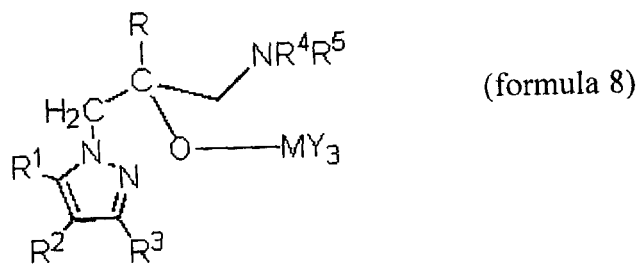     (formula 8)

Signed and Sealed this
Eighth Day of February, 2011

David J. Kappos
*Director of the United States Patent and Trademark Office*